United States Patent [19]
Hobbs

[11] Patent Number: 5,153,141
[45] Date of Patent: Oct. 6, 1992

[54] METHOD OF DETERMINING PH BY THE ALKALINE ABSORPTION OF CARBON DIOXIDE

[76] Inventor: David T. Hobbs, 1867 Lodgepole Ave., N. Augusta, S.C. 29841

[21] Appl. No.: 754,840

[22] Filed: Sep. 4, 1991

[51] Int. Cl.[5] .......................................... G01N 21/75
[52] U.S. Cl. ...................................... 436/168; 436/34; 436/131; 436/133; 436/163; 436/167; 73/61.41; 73/19.1
[58] Field of Search ............... 436/131, 163, 167, 168, 436/133, 34; 73/61 R

[56] References Cited

U.S. PATENT DOCUMENTS

| | | | |
|---|---|---|---|
| 751,897 | 2/1904 | Bodlander. | |
| 3,660,034 | 2/1972 | Baranyi et al. | 23/230 |
| 3,716,337 | 2/1973 | Jones | 436/133 X |
| 3,867,097 | 2/1975 | Vurek | 23/254 |
| 4,663,724 | 5/1987 | Onizuka et al. | 436/133 X |
| 4,677,060 | 6/1987 | Valet et al. | 435/29 |
| 4,851,195 | 7/1989 | Matthews et al. | 422/68 |

*Primary Examiner*—James C. Housel
*Assistant Examiner*—Maureen M. Wallenhorst
*Attorney, Agent, or Firm*—Harold M. Dixon; William R. Moser; Richard E. Constant

[57] ABSTRACT

A method for measuring the concentration of hydroxides in alkaline solutions in a remote location using the tendency of hydroxides to absorb carbon dioxide. The method includes the passing of carbon dioxide over the surface of an alkaline solution in a remote tank before and after measurements of the carbon dioxide solution. A comparison of the measurements yields the absorption fraction from which the hydroxide concentration can be calculated using a correlation of hydroxide or pH to absorption fraction.

6 Claims, 1 Drawing Sheet

METHOD OF DETERMINING PH BY THE ALKALINE ABSORPTION OF CARBON DIOXIDE

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention:

The present invention relates to the absorption of carbon dioxide by alkaline solutions. In particular, the present invention relates to the use of the absorption of carbon dioxide by alkaline solutions for the determination of pH or hydroxide concentration in an inaccessible location.

2. Discussion of Background:

It is known that alkaline solutions will absorb carbon dioxide. Methods for measuring carbon dioxide concentrations, and apparatus for implementing those methods, are described in the relevant literature. For example, Matthews, et al., in U.S. Pat. No. 4,185,195, describe a sensor for determining the partial pressure of carbon dioxide in a liquid by determining the pH of that liquid and inferring the $CO_2$ concentration. The liquid, preferably a transparent aqueous gel, exhibits variations in pH as a function of the partial pressure of dissolved $CO_2$.

In U.S. Pat. No. 3,660,034, Baranyi, et al., disclosed an apparatus and process for determining the maturity of fruit by absorbing, into an alkaline solution, the amount of $CO_2$ developed by the fruit as its carbohydrates break down, then measuring the changes in electrical conductivity of the solution.

Under certain circumstances, it is not feasible or desirable to measure the pH or the carbon dioxide concentration of a solution. For example, the solution may be located in a remote area, where direct access to the solution for sampling is difficult or time-consuming, or the solution may be toxic or radioactive. Minimizing personnel exposure to hazardous solutions may be a legal requirement as well as, of course, a legitimate management concern. Thus, there are situations where the solution is inaccessible but concentration information about it is needed.

In industrial process control, where laboratory conditions do not exist and miscellaneous conditions that might affect the process cannot always be controlled, a correlation used to calculate a variable such as concentration by inference from measured values must be sufficiently accurate and the measurements must be easily and rapidly obtained. There is a need, then, for a method for determining the pH and hydroxide concentrations of solutions, remotely and accurately, especially when the solutions are hazardous or otherwise inaccessible.

SUMMARY OF THE INVENTION

According to its major aspects and broadly stated, the present invention is a method for determining remotely the hydroxide content or pH of a solution from known carbon dioxide concentrations. In the particular embodiment of determining the hydroxide concentration or pH of a solution, the method comprises the steps of making a first measurement of the concentration of a quantity of carbon dioxide, such as that naturally contained in air, then passing the air with the carbon dioxide over the solution to expose it to the solution during a time interval. A portion of the carbon dioxide is absorbed by the solution. Then a second measurement of the concentration of the carbon dioxide is made to compare to the first measurement. The absorption fraction of carbon dioxide is determined, and, from that fraction, the concentration of hydroxide or pH. The first and final measurements can be made remotely with respect to the location of the solution, not in the tank containing the solution, but, rather, at a safe distance therefrom. The air, or other carrier gas, is pumped to and from the remote location.

The passing of $CO_2$, whether carried by a gas or not, across the alkaline solution, is an important feature of the present invention because this feature means that it is possible to pump the $CO_2$, with carrier gas, in a once-through mode, thereby allowing the pre- and post-measurements to be done at a distance from the tank where the alkaline solution is stored. If the alkaline solution is hazardous, or the $CO_2$ or its carrier gas is hazardous, the reaction will minimize personnel contact and exposure.

The speed of the reaction between $CO_2$ and the alkaline solution is an important feature of the present invention. The reaction kinetics are extremely fast and enable measurements to be done in rapid succession. If the $CO_2$ measurements are fed directly into a programmed general purpose computer or dedicated computer, the results approach real-time speed. For processes where hydroxide concentration or pH must be tightly controlled, that is, an abrupt change in hydroxide concentration or pH must be responded to quickly, the present method is ideal.

The correlation between $CO_2$ absorption fraction and hydroxide concentration or pH is another important feature of the present invention. The correlation is accurate, as indicated by a correlation coefficient from linear regression analysis of sample data of 0.948. For most industrial processes and certainly as a tool for alerting an operator that a hydroxide concentration may be going out of tolerance, the correlation is sufficiently accurate. Moreover, in the case of radioactive solutions, where the number of sample measurements taken by workers should be reduced, the present method eliminates the need for all but confirmatory measurements.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Alkaline solutions readily absorb carbon dioxide forming bicarbonate and carbonate species as shown in equations 1 and 2:

$$CO_2 + OH^- = HCO_3 - (aq) \qquad \text{Equation 1:}$$

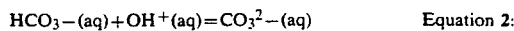

$$HCO_3 - (aq) + OH^+(aq) = CO_3{}^2 - (aq) \qquad \text{Equation 2:}$$

Alkaline solutions will absorb $CO_2$ directly from the air, or other carrier gas. The rate of absorption is based on the concentration of hydroxide in solution primarily and, to a lesser extent, on other factors.

The present invention is a method for using the reaction relationships of Equations 1 and 2 to determine the concentration of, in a first embodiment, hydroxide using measurements of $CO_2$ before and after it has passed over the alkaline solution.

Figure 1:
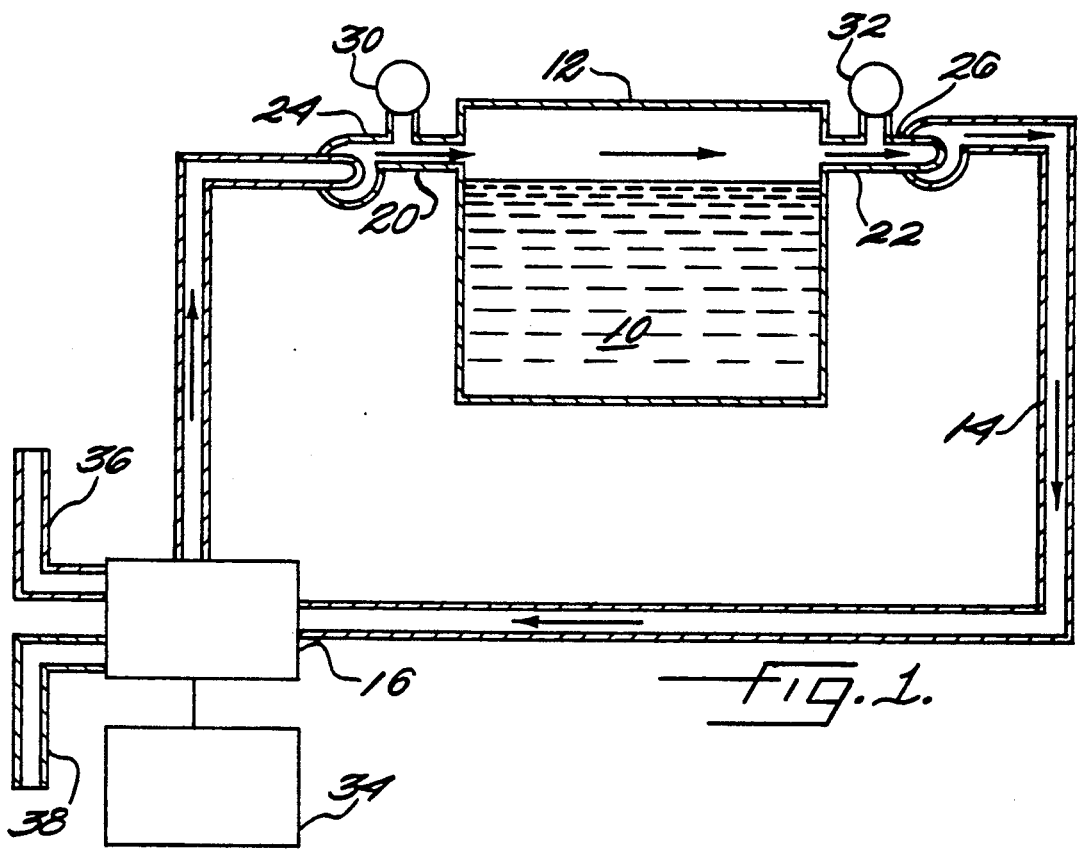
FIG. 1 is a schematic diagram of a process system according to a preferred embodiment of the present invention.

In illustration of the first of the two embodiments, as depicted schematically in FIG. 1, an alkaline solution 10 is stored in a process tank 12. At a location remote from the solution, but in fluid communication with the space in tank 12 above the solution via piping 14, is a source 16 of carbon dioxide. The carbon dioxide provided by source 16 may be carried by a carrier gas, preferably air if alkaline solution 10 does not react in significant ways with air or its other constituents. Most preferably, the carrier gas is air and the $CO_2$ is supplied by the naturally occuring $CO_2$ component of air, this source being the most economical and, by and large, both sufficient in its amount of $CO_2$ and in stability so as to serve as an appropriate source.

To begin the process, measurements are made of the instantaneous atmospheric carbon dioxide levels. The measurements of $CO_2$ concentration before and after the passing of the $CO_2$ across the surface of the alkaline solution is done at or near the tank inlet 20 and outlet 22, allowing sufficient time for stabilization before recording each measurement. Flow rates are measured using appropriate flowmeter gauges in tank.

Pumps 24 and 26 move a quantity of the $CO_2$ into the atmosphere of tank 12 through inlet 20, across the surface of solution 10, and out exit 22. While moving relative to solution 10, the $CO_2$ is absorbed from the air in part by the liquid phase of the hydroxides of solution 10, removing the $CO_2$ from the carrier gas and reacting instantaneously to form bicarbonate. When sufficient hydroxide is present in solution 10, the bicarbonate reacts with additional hydroxide to form carbonate. Carbon dioxide is continually absorbed until the partial pressure of carbon dioxide in equilibrium with the liquid phase equals the partial pressure of carbon dioxide in the air entering the tank. Thus the concentration of $CO_2$ will decrease from that entering tank 12 to that leaving the tank 12. A measurement of the $CO_2$ concentration before and after exposure to solution 10 in tank 12 can be used to determine the fraction of $CO_2$ absorbed.

$CO_2$ measurements can be done, for example, using a MIRAN ™ 101 gas analyzer made by Foxboro. For best results, the analyzer is first zeroed with purified nitrogen and calibrated with two different, calibrated carbon dioxide standards before each measurement. This particular monitoring instrument is portable and the technique is rapid, requiring less than one hour to perform the calibration and determine the $CO_2$ absorption fraction of eight different tanks. Gas analyzers can be positioned anywhere outside tank 12, such as analyzers 30 and 32.

Controlling source 16 to assure that the air supply is fresh is a controller 34 which opens valving of conventional design to an inlet 36 and an exit 38 to the atmosphere. Controller 34 may also be in operative communication with pumps 24 and 26 and analyzers 30, 32.

The absorption fraction is calculated by dividing the difference of the carbon dioxide concentrations entering and exiting the tank by the carbon dioxide concentration entering the tank as shown in Equation 3:

Absorption Fraction
= {[$CO_2$]enter − [$CO_2$]exit}/[$CO_2$]enter     Equation 3

The initial hydroxide concentration or pH of the alkaline solution correlates with the amount of $CO_2$ it will absorb. The rate of absorption and the absorption fraction do not seem to correlate with time-of-day, date, atmospheric carbon dioxide concentration, wind direction, wind speed, temperature or air flow rate. The insensitivity of the absorption fraction to air flow rate and carbon dioxide concentration may reflect the limited range of these variables in developing the correlations. Higher correlation coefficients were observed for nitrate concentration, specific gravity and, of course, hydroxide concentration (pH).

The highest correlation observed was between the hydroxide concentration or pH of the solution and the absorption fraction, pH being defined by Equation 4:

$$pH = 14 + \log[OH^-]$$     Equation 4

The correlation found is shown in Equation 5:

Absorption Fraction $= 0.165\, pH - 1.569$     Equation 5

Figure 2:
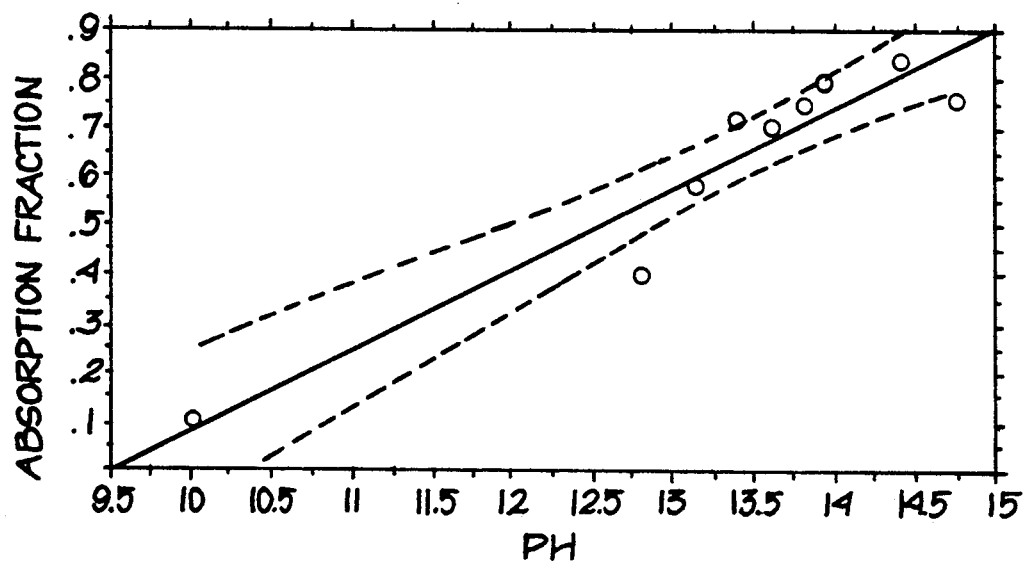
FIG. 2 is a graph showing the correlation of absorption concentration versus pH.

The function defined by Equation 5 is depicted graphically in FIG. 2. It will be seen from Equations 4 and 5 that the correlation is linear between the fraction of $CO_2$ absorbed and the logarithm of the hydroxide concentration. The correlation coefficient from the linear regression analysis used to develop Equation 5 is 0.948. Hydroxide concentration can then be given by Equation 6:

$$[OH^-] = 10^{[(Absorption\ Fraction - 0.741)/0.165]}$$     Equation 6

The rate of absorption is calculated by multiplying the flow rate by the concentration of $CO_2$ in the air and then by the absorption fraction.

It will be apparent to those skilled in the art that many changes and substitutions can be made to the preferred embodiment herein described without departing from the spirit and scope of the present invention as defined by the appended claims.

What is claimed is:

1. A method for measuring hydroxide concentration or pH of a solution, said method comprising the steps of:
   making a first measurement of the concentration of a quantity of carbon dioxide; carried by a gas
   passing said gas over said solution to expose said carbon dioxide to said solution during a time interval, whereby a portion of said quantity is absorbed by said solution;
   making a second measurement of the concentration of said quantity of carbon dioxide in the gas after exposure to said solution;
   comparing said first measurement to said second measurement to determine a rate of carbon dioxide absorption; and
   calculating the concentration of hydroxide or pH of said solution from said rate.

2. The method as recited in claim 1, wherein said solution is at a first location and said carbon dioxide is initially at a second location separated from said first location, said method further comprising the steps of:
   pumping said quantity of carbon dioxide from said second location to said first location at the beginning of said time interval; and pumping said exposed quantity of carbon dioxide from said first location to said second location at the end of said time interval.

3. The method as recited in claim 1, wherein said carbon dioxide is carried by air.

4. A method for measuring hydroxide concentration or pH of a hazardous solution, said method comprising the steps of:

making a first measurement of the concentration of a quantity of carbon dioxide; carried by a gas passing said gas over said solution to expose said carbon dioxide to said solution during a time interval, whereby a portion of said quantity is absorbed by said solution;

making a second measurement of the concentration of said quantity of carbon dioxide in the gas after exposure to said solution;

comparing said first measurement to said second measurement to determine a rate of carbon dioxide absorption; and calculating the concentration of hydroxide or pH of said solution from said rate.

5. The method as recited in claim 4, wherein said solution is at a first location and said carbon dioxide is initially at a second location isolated from said first location, said method further comprising the steps of:

pumping said quantity of carbon dioxide from said second location to said first location at the beginning of said time interval; and pumping said exposed quantity of carbon dioxide from said first location to said second location at the end of said time interval.

6. The method as recited in claim 4, wherein said carbon dioxide is carried by air.

* * * * *